United States Patent [19]
Weinstock

[11] Patent Number: 5,423,223
[45] Date of Patent: Jun. 13, 1995

US005423223A

[54] FATIGUE DETECTION IN STEEL USING SQUID MAGNETOMETRY

[75] Inventor: Harold Weinstock, Springfield, Va.
[73] Assignee: The United States of America as represented by the Secretary of the Air Force, Washington, D.C.
[21] Appl. No.: 17,196
[22] Filed: Feb. 12, 1993
[51] Int. Cl.[6] .............................................. G01N 3/32
[52] U.S. Cl. ........................................ 73/810; 73/811; 73/577; 73/779; 324/209
[58] Field of Search ................ 73/808, 812, 813, 779, 73/815, 577, 578, 810, 811; 324/209, 248

[56] References Cited

U.S. PATENT DOCUMENTS

| | | | |
|---|---|---|---|
| 3,564,903 | 2/1971 | Woodmansee et al. | 73/582 |
| 3,699,808 | 10/1972 | Ford et al. | 73/779 |
| 4,048,847 | 9/1977 | Alers et al. | 73/812 |
| 4,179,940 | 12/1979 | Oertle et al. | 73/808 |
| 4,906,607 | 3/1990 | Dev Tyagi | 324/248 |
| 4,931,729 | 6/1990 | Pratt | 324/209 |
| 5,010,299 | 4/1991 | Nishizawa et al. | 324/209 |
| 5,086,651 | 2/1992 | Westermo et al. | 73/763 |
| 5,105,667 | 4/1992 | Satoh et al. | 73/862.36 |
| 5,173,660 | 12/1992 | Mardsen | 324/248 |

*Primary Examiner*—Hezron E. Williams
*Assistant Examiner*—Nashmiya Ashraf
*Attorney, Agent, or Firm*—Donald J. Singer; Irwin P. Garfinkle; William G. Auton

[57] ABSTRACT

The magnetoelectric coefficient in iron-based alloys has a stress value of about 0.6 of that of the elastic limit. A reversal in sign is caused by structural phase slip which is the basis for the onset of metal fatigue. Based on this phenomenon, a method is provided for determining the onset of metal fatigue. The method includes applying a periodic mechanical stimulus at a given frequency to a test structure, and using a magnetometer, sensing the magnetic field of said structural element during the application of stimulus, and then determining whether or not there is a 180 degree difference between the phase of the stimulus and that of the magnetic response for various regions of the test structure.

13 Claims, 1 Drawing Sheet

FATIGUE DETECTION IN STEEL USING SQUID MAGNETOMETRY

STATEMENT OF GOVERNMENT INTEREST

The invention described herein may be manufactured and used by or for the Government for governmental purposes without the payment of any royalty thereon.

FIELD OF THE INVENTION

The purpose of this invention is to detect mechanical fatigue in structural elements containing iron-based alloys (generally steel) prior to the evolution of visible cracks, ruptures or other defects. Once visible defects occur, collapse or failure of a structure can proceed quite rapidly, often with catastrophic results. In being able to determine a physical state of a structural member which is indicative of phase slip at a microscopic level, one knows that the process of metal fatigue already has begun. The precursor to structural failure can then be utilized to have the fatigued element strengthened or replaced before a serious problem develops.

This invention is for a method of detecting fatigue in steel by using SQUID Magnetometry. The magnetoelastic coefficient in iron-based alloys has a sign reversal at a stress value approximately 0.6 of that of the elastic limit. The SQUID magnetometer is employed to survey the surface and interior of a structural element while the element is subjected to low-level periodic vibration. By activating a periodic electromechanical transducer on a steel structural element, the phase of the magnetic response of a SQUID magnetometer placed nearby will indicate if the element is in a fatigued state.

BACKGROUND OF THE INVENTION

A variety of methods have been used to detect flaws in metallic structural materials. Where surfaces are exposed, visual inspection is employed, sometimes with the aid of a fluid which makes minute cracks readily visible in the presence of ultraviolet light.

Other methods of nondestructive evaluation (NDE) employ ultrasonic waves, light scattering, eddy currents and x-rays. All of these methods involve the possible detection of some path deviation of an imposed physical wave phenomenon, either electromagnetic or mechanical in nature. Some of these are portable for use in the field, but just about all of the methods require intimate proximity to the element under test, e.g., ultrasonic NDE techniques require physical contact to the element under test. Other techniques, such as thermal wave imaging and eddy current excitation are effective only within a small depth of the surface. Most techniques are not effective at determining defects well within the interior of a structure. While x-ray analysis is an exception to this, it is not practical to place the most sensitive x-ray equipment near a test element in the field. Also, because fatigue originates in an atomic level phase slip process, it is difficult for any existing technique to detect fatigue in its earliest stages.

This invention makes use of (1) my earlier discovery of a phenomenon unique to iron-based alloys and (2) the extreme sensitivity of SQUID magnetometry to minute changes in magnetic field. It employs also the principle of phase sensitive detection so that small changes in a magnetic field surrounding an iron-containing structure can be related to atomic reorientation within that structure without being masked by unrelated environmental magnetic noise of a larger magnitude.

Phase sensitive detection requires that a periodic mechanical stimulus be applied to the test structure. The output circuit of the SQUID magnetometer is operated at the same frequency as that of the mechanical stimulus, and its phase is adjusted to produce a maximum response. If the phase of the magnetic response is the same as that of the mechanical stimulus (exclusive of fixed internal electronic phase shifts), then this indicates that the magnetic field due to stress within the structure is increasing when the stress is increased by an incremental amount. This is the situation that occurs when the total stress within elements of the structure is less than about 60% of that which produces plasticity, i.e., less than 60% of the elastic limit stress. If the magnetic response is 180° out of phase with the periodic mechanical stimulus, then it is known that the threshold level for atomic phase slip and subsequent fatigue has been exceeded.

THE PRIOR ART

A number of patents were noted in a search of the prior art:

These patents relate to methods and apparatus for measuring strain or fatigue. None shows the inventive concepts of this invention.

U.S. Pat. No. 5,105,667, to Satoh et al is directed to a strain measuring device which comprises a passive member, a magnetic shielding layer, a magnetostrictive layer and a permeability detection means. The passive member is of ferromagnetic material, and is provided to receive an external force. The magnetic shielding layer covers the surface of the passive member and shields the passive member from magnetic influences. The magnetostrictive layer is formed on the shielding layer in short strip-like elements with high magnetic permeability which varies as a function of the external force. The permeability detection means which is located around the magnetostrictive layer, subjects the layer to a magnetic flux, and detects changes in magnetic permeability in the magnetostrictive layer caused by strain due to the external force.

U.S. Pat. No. 5,086,651 to Westermo et al describes a strain monitoring apparatus. The apparatus utilizes a material which undergoes a phase change from a non-ferromagnetic state to a ferromagnetic state in response to strain. The material is secured to a structural element so that relative movement between the securing mounts resulting from stress on the structure places strain on the material. Instrumentation measures the phase change so that the degree of phase change may be used to calculate the strain on the structural element.

U.S. Pat. No. 5,010,299 to Nishizawa et al relates to a method for measuring stress in steel material. According to the Nishizawa, the reversible magnetic permeability is determined by using a stress detector of steel materials utilizing the phenomenon of magnetostriction under a magnetic bias field. With this value for the magnetic permeability the first order factor for the reversible magnetic permeability of the steel material is then calculated. The value of a principal stress in the steel material can then be calculated from the previously measured and calculated values.

U.S. Pat. No. 4,931,729 to Pratt is directed to an apparatus for measuring strain or fatigue, which operates on the principle that the time required for the magnetic domain to flip orientation within a ferromagnetic material varies with stress or fatigue within the material. The apparatus is connected to external electrical circuitry, which includes a timing apparatus, under a zero stress condition. The magnetic pulse wave transversing the ferromagnetic material is measured as a discrete time interval. When stress is applied to the conductive element, the magnetic domain orientation flip time of the domains within the ferromagnetic material changes, causing a change in the measured discrete time interval. The change in the magnetic domain flip time is directly proportional to the stress within the ferromagnetic material and to the stress within a substrate to which the apparatus is attached.

Although each of these patents relates to methods and apparatus for measuring strain or fatigue, they do not describe a method using magnetometry to determine the sign reversal of the magnetoelastic coefficient (i.e., magnetic flux versus strain) in an iron based alloy under strain as an indication of fatigue.

SUMMARY OF THE INVENTION

The magnetoelectric coefficient in iron-based alloys has a reversal of sign at a stress value of about 0.6 of that of its elastic limit. This reversal in sign is caused by structural phase slip which is the basis for the onset of metal fatigue. Based on this phenomenon, a method and system are provided for determining the onset of metal fatigue. The method includes applying a periodic mechanical stimulus at a given frequency to a test structure, and using a magnetometer, sensing the magnetic field response of said structural element during the application of a stimulus, and then noting whether this response is in or out of phase with the given stimulus over various regions of the test structure.

DESCRIPTION OF THE PREFERRED EMBODIMENT OF THE INVENTION

Figure 1:
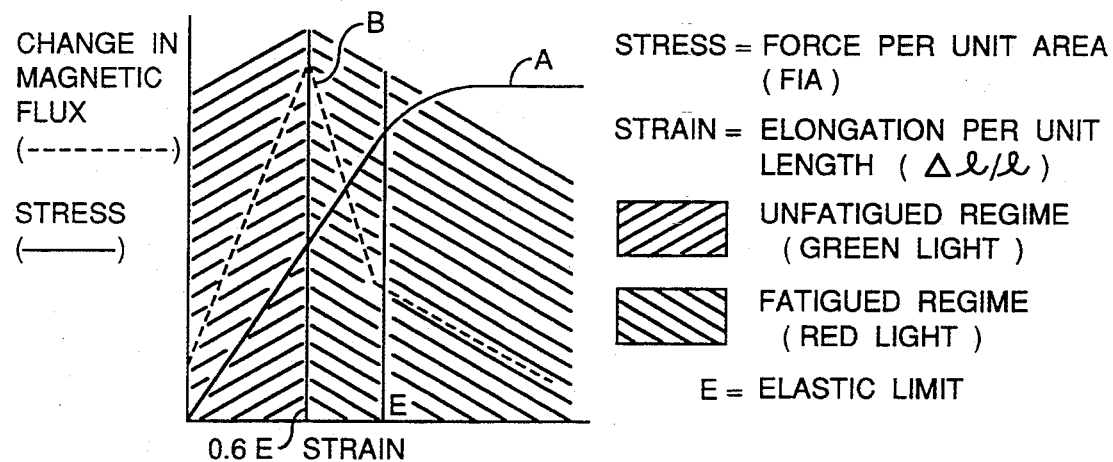
FIG. 1 is a plot showing the change in detected magnetic flux versus the level of strain in a test structure.

FIG. 1 shows schematically the magnetic field and the stress responses applied to a steel bar. The solid A line shows the force per unit area. The dotted B line shows the change in magnetic flux versus strain (elongation per unit of length). It will be noted that when a steel alloy has been strained to 60% of its elastic limit, the sign of the slope of the magnetic flux changes. It has been determined that it is at this point, that steel alloy elements are fatigued, and should either be re-inforced or replaced before failure. The object of this invention is to determine whether or not the 60% condition has been reached or exceeded.

Figure 2:
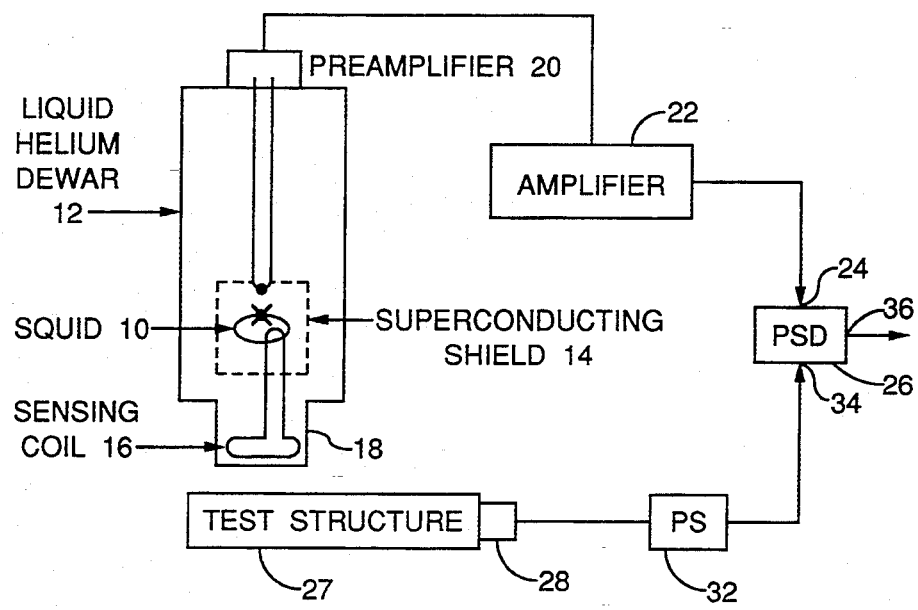
FIG. 2 is a schematic of the apparatus used in accordance with this invention.

The apparatus shown in FIG. 2 is used to carry out the method of this invention. As shown in FIG. 2, the apparatus includes a known SQUID magnetometer 10 housed in a liquid helium dewar container 12. The magnetometer is shielded by superconducting shield 14. The sensing coil 16 of the magnetometer is located within a projection 18 of the dewar container.

The sensed output of the magnetometer 10 is applied to a preamplifier 20 and then to an amplifier 22. The output of the amplifier 22 is applied to the first input 24 of a phase sensitive detector 26. The sensing coil 16 is shown positioned adjacent to a steel structure 27 which is under test for potential fatigue. An electromechanical transducer 28, powered by a power supply 32 at a selected stimulus frequency which serves to vibrate the test structure at that frequency. The selected stimulus frequency of the power supply is applied to the phase sensitive detector 26 at its second input terminal 34.

The output 36 of the phase sensitive detector provides an indication of the degree of the strain. If the degree of strain exceeds 60% of the strain at the elastic limit, the phase of the magnetic field detected by the magnetometer changes by 180 degrees with respect to the phase of the stimulus frequency. If the strain is below the 60% level the stimulus frequency and the detected magnetometer signals will be in phase. In a simple case, the signal phase may be converted to the illumination of a green light for a safe condition or a red light for a dangerous condition.

The simplicity of this invention is that it requires no calibration to determine whether a structural element is at risk of experiencing some form of mechanical failure. For example, when the response and stimulus are in phase, a green light would illuminate; when the phase difference is 180°, a red light (indicating a problem) would illuminate. The magnetic field external to the element under test at any position in the vicinity of that element is the vector sum of the contribution from all atomic magnetic moments (generally arranged in aligned aggregates of at least $10^{11}$ atoms forming magnetic domains) throughout the interior of the element, with those atoms closest to the position of the magnetic field sensor having the greatest contribution. Thus, one would use the sensor to survey the surface and interior of the structure in question, paying particular attention to those regions, e.g., joints and smaller cross-section areas, where stress levels are known to be highest. However, the great virtue of utilizing superconducting sensing coils coupled to a SQUID magnetic flux sensor is that the extreme magnetic flux sensitivity of this system makes it unnecessary for the sensing coils, or more precisely the outer surface of the cryogenic dewar containing the sensing coils to be in intimate contact with the surface of the test structure. For greater coverage and/or faster surveying, this concept can be extended to an array of SQUIDS and associated sensing coils.

This means that if it is possible to provide a periodic mechanical stimulus to a structure, it is still possible to detect fatigue within an interior section of the structure which contains some fraction of iron atoms. Specifically, this would apply to steel-reinforced concrete, steel pipes that are buried or insulated with some other material, or structures so configured that a sizable air gap is required between sensor and test structure.

Referring again to FIG. 1, it is noted that there is a qualitative change in slope of the magnetic response to strain when the structure enters the region of plastic flow (beyond the elastic limit). This observation could be utilized in a stress-sensing SQUID magnetometer system, but require a calibration for specific geometries and types of structures with prescribed separations of sensor and structure.

Basically, this invention allows for contactless sensing of fatigue in ferromagnetic (specifically iron-based) materials and in a manner that does not require instrument calibration. The extreme sensitivity of SQUID magnetometry (2 or 3 orders of magnitude more sensitive than any competing commercial instrument) permits sensing at a distance, while the unique magnetomechanical response of iron-based alloys, which is keyed to the onset of fatigue, permits one to construct a testing system which provides an unambiguous qualitative indication of the presence of metal fatigue.

While the qualitative discovery of metal fatigue is limited to those structural elements composed of iron or iron-based alloys, it will be possible to detect the presence of small structural defects by surveying with a SQUID magnetometer non-ferrous elements which carry electric current. The magnetic field associated with the current flow will have an anomalous behavior near a region in which the current is forced to alter its uniform flow because of a structural defect. When a low frequency alternating current is employed, a related time-varying magnetic field will be associated with it, thus making phase-sensitive detection possible and filtering out environmental magnetic fields due to other sources.

Although the invention has been described with reference to a particular embodiment, it will be understood to those skilled in the art that the invention is capable of a variety of alternative embodiments within the spirit and scope of the appended claims.

What is claimed is:

1. A method for the detection of mechanical fatigue in a structural element which has an elastic limit and which contains iron-based alloys prior to evolution of visible defects, comprising the steps of:
    applying an applied stimulus which comprises a periodic mechanical stimulus with a phase at a given frequency to said structural element to induce a magnetic field in said structural element;
    sensing said induced magnetic field with a magnetometer during the application of said periodic mechanical stimulus, said magnetometer producing an output with a phase;
    comparing the phase of the output of the magnetometer with the phase of the applied stimulus;
    determining whether the applied stimulus and the output of said magnetometer are in phase or out of phase; and
    designating a presence of mechanical fatigue in said structural element when the output of the magnetometer and the applied stimulus are out of phase to an extent indicative of a stress value of 0.6 of the elastic limit of the structural element.

2. The method of claim 1, and the additional steps of:
    generating a first signal when the output of said magnetometer is in phase with the applied periodic stimulus, said first signal representing a safe condition in said structural element; and
    generating a second signal when the output of the magnetometer is out of phase with the applied periodic stimulus, said second signal representing an unsafe condition in said structural element.

3. The method of claim 1 wherein the magnetometer is housed in a cryogenic container.

4. The method of claim 1, and adjusting of the applied stimulus frequencies and phase relations to produce a maximum signal response.

5. The method of claim 3, and shielding said magnetometer with a superconducting shield.

6. A system for the detection of mechanical fatigue in a structural element which has an elastic limit and which contains iron-based alloys prior to evolution of visible defects, said system comprising:
    means for applying an applied stimulus which comprises a periodic mechanical stimulus with a phase at a given frequency to said structural element to induce a magnetic field with a phase in said structural element;
    means for sensing said induced magnetic field of said structural element during the application of said periodic mechanical stimulus;
    means for comparing the phase of the induced magnetic field with the phase of the applied stimulus; and
    means for determining whether the phase of the applied periodic stimulus and the phase of the induced magnetic field are in phase or out of phase, said determining means and said comparing means indicating a presence of mechanical fatigue in said structural element when the phase of the induced magnetic field is out of phase with the phase of the applied stimulus indicative of a stress value of 0.6 of the elastic limit of the structural element.

7. The system of claim 6, and means for generating a first signal when the induced magnetic field is in phase with the applied periodic stimulus, said first signal representing a safe condition in said structural element; and
    means for generating a second signal when the induced magnetic field is out of phase with the applied periodic stimulus, said second signal representing an unsafe condition in said structural element.

8. The system of claim 7 wherein said sensing means is spaced from said structural element in close proximity thereto.

9. The system of claim 8 wherein a phase reversal in said induced magnetic field occurs whenever said structural element has been strained more than 60% of the elastic limit of the structural element.

10. The system of claim 6 wherein said sensing means is a magnetometer.

11. The system of claim 10 wherein said magnetometer is spaced from said structural element in close proximity thereto.

12. The system of claim 10, wherein said magnetometer is a SQUID and is housed in a cryogenic container.

13. The system of claim 12, and a superconducting shield for shielding said magnetometer.

* * * * *

UNITED STATES PATENT AND TRADEMARK OFFICE
CERTIFICATE OF CORRECTION

PATENT NO. : 5,423,223
DATED     : 13 June 1995
INVENTOR(S) : HAROLD WEINSTOCK

It is certified that error appears in the above-identified patent and that said Letters Patent is hereby corrected as shown below:

In the Abstract on Page 1, line 1, the word "magnetoelectric" should read -- magnetoelastic --, and after "has" please add -- a reversal in sign at --.

Signed and Sealed this

Seventeenth Day of October, 1995

Attest:

BRUCE LEHMAN

*Attesting Officer*          *Commissioner of Patents and Trademarks*